United States Patent [19]

Schumacher et al.

[11] Patent Number: 5,023,335
[45] Date of Patent: Jun. 11, 1991

[54] 1,2-BIS (AMINOMETHYL) CYCLOBUTANE-PLATINUM COMPLEXES

[75] Inventors: Wolfgang Schumacher, Mannheim; Johannes Respondek, Hanau; Jürgen Engel, Alzenau; Jörg Pohl, Halle; Rainer Voegeli; Peter Hilgard, both of Bielefeld, all of Fed. Rep. of Germany

[73] Assignee: ASTA Pharma Aktiengesellschaft

[21] Appl. No.: 590,610

[22] Filed: Sep. 25, 1990

Related U.S. Application Data

[63] Continuation of Ser. No. 295,072, Jan. 9, 1989, abandoned.

[30] Foreign Application Priority Data

Jan. 9, 1988 [DE] Fed. Rep. of Germany ....... 3800415

[51] Int. Cl.$^5$ .................. C07D 25/00; C07F 15/00
[52] U.S. Cl. .................... 548/104; 556/137; 548/953; 548/403
[58] Field of Search ............. 556/137; 514/442; 548/953, 104, 403

[56] References Cited

U.S. PATENT DOCUMENTS

| | | | |
|---|---|---|---|
| 4,322,362 | 3/1982 | Kaplan et al. | 260/429 R |
| 4,410,544 | 10/1983 | Berg et al. | 556/137 |
| 4,482,569 | 11/1984 | Butler et al. | 556/137 |

FOREIGN PATENT DOCUMENTS

| | | |
|---|---|---|
| 0055300 | 7/1982 | European Pat. Off. . |
| 0166366 | 1/1986 | European Pat. Off. . |
| 0181166 | 5/1986 | European Pat. Off. . |
| 0185225 | 6/1986 | European Pat. Off. . |
| 0237450 | 9/1987 | European Pat. Off. . |
| 0290169 | 11/1988 | European Pat. Off. . |
| 1618050 | 1/1970 | Fed. Rep. of Germany . |
| 214505 | 10/1985 | New Zealand . |
| 1432562 | 4/1976 | United Kingdom . |
| 2024823 | 1/1980 | United Kingdom . |
| 2066819A | 7/1981 | United Kingdom . |

OTHER PUBLICATIONS

Von Alessandro Pasini and Franco Zunion, "Neue Cis-platin-Analoga–" auf dem Weg zu besseren Cancero-statica, Angew Chem 99 (1987) pp. 632–641 (translation also attached).

Larry M. Hall, Robert J. Speer, Helen J. Ridgway, David P. Stewart, Andrew D. Newman and Joseph M. Hill, "Analogs of Sulfato 1,2-Diaminocyclohexane Platinium (II) (SHP) II, Modifications Other Than Leaving Ligand", Analogs of SHP: Non Leaving Ligands, vol. 7, No. 1, pp. 231–241.

*Primary Examiner*—Gary P. Straub
*Assistant Examiner*—Stuart L. Hendrickson
*Attorney, Agent, or Firm*—Cushman, Darby & Cushman

[57] ABSTRACT

1,2-Bis(aminomethyl)-cyclobutane-platinum complexes having an anti-tumor activity.

13 Claims, No Drawings

1,2-BIS (AMINOMETHYL) CYCLOBUTANE-PLATINUM COMPLEXES

This is a continuation of application Ser. No. 07/295,072 filed on Jan. 9, 1989 which was abandoned upon the filing hereof.

The present invention relates to platinum compounds useful for the treatment of cancer, and having low toxicity.

BACKGROUND OF THE INVENTION

British patent application No. 2,024,823 discloses, for example, platinum complexes of 1,1-bis(aminomethyl)-cyclobutane. These compounds are recommended for the treatment of cancer.

SUMMARY OF THE INVENTION

The object of the present invention is to provide compounds which have good antitumor activity (for example in vitro against AH 135-tumor, B 16-melanoma, colon 115; in vivo for example against P 388 leukaemia in the mouse). In addition the compounds of the invention display only a low toxicity. In particular, they do not have cumulative toxicity or nephrotoxicity. Furthermore, bone marrow toxicity is low and the feared thrombocytopaenia does not occur.

In addition, the compounds of the invention are surprisingly readily soluble in water.

These and other objects are achieved with 1,2-bis-(aminomethyl)cyclobutane-platinum complexes having the general formula

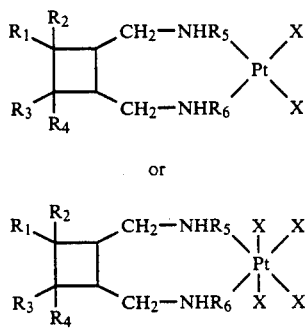

wherein the radicals $R_1$, $R_2$, $R_3$, $R_4$, $R_5$ and $R_6$ are the same or different and represent hydrogen, $C_1$-$C_6$-alkyl, phenyl, phenyl-$C_1$-$C_6$-alkyl, $C_1$-$C_6$-alkyl which is substituted by halogen, hydroxy, $C_2$-$C_6$-alkanoyloxy or $C_1$-$C_6$-alkoxy, phenyl which is substituted by halogen, hydroxy, $C_2$-$C_6$-alkanoyloxy or $C_1$-$C_6$-alkoxy or phenyl-$C_1$-$C_6$-alkyl which is substituted in the phenyl moiety by halogen, hydroxy, $C_2$-$C_6$-alkanoyloxy or $C_1$-$C_6$-alkoxy and X represents the equivalent of a physiologically acceptable anion or X represents a water molecule and in this case the existing positive charge of the platinum atom is also neutralized by a physiologically acceptable anion, and salts thereof.

The following are preferred embodiments of the invention:

The $C_1$-$C_6$-alkyl groups, alkoxy groups and the $C_2$-$C_6$-alkanoyloxy groups can be straight or branched. The alkyl or alkoxy groups preferably consist of 1 to 4 carbon atoms, the alkanoyloxy groups preferably of 2 to 4 carbon atoms. This also applies when $C_1$-$C_6$-alkyl groups are a component of other functional groups. The alkanoyloxy group may in particular be the acetoxy group. The halogen substituents may in particular be bromine, chlorine and/or fluorine. In the case of the phenyl-$C_1$-$C_6$-alkyl group, the alkyl portion preferably consists of one, two or three carbon atoms. This is preferably the benzyl group or the 1-phenylethyl group, the phenyl portion being optionally substituted as stated in each case.

Phenyl radicals may be mono-, di- or tri-substituted by the radicals mentioned, which may be the same or different, for example such a phenyl radical may contain 1 or 2 halogen atoms (such as chlorine) preferably in the 2- and/or 6-positions as well as, in addition, a hydroxy group (preferably in the 4-position).

A particularly favorable effect is displayed by those compounds of formula I' or I" in which all radicals $R_1$ to $R_6$ represent hydrogen or in which the radicals $R_1$ to $R_4$ are hydrogen and one or both of radicals $R_5$ and/or $R_6$ represent $C_1$-$C_4$-alkyl group, in particular a methyl group.

The radicals X, which may be the same or different, represent the known, conventional physiologically acceptable and pharmaceutically useful anions of single or multivalent acids or also the hydroxy anion ($OH^-$). Should such acids have asymmetrical carbon atoms, these may be present as racemates, as optically pure forms or in the form of the corresponding diastereomers. The anions of the following acids are for example particularly suitable: HBr, HCl, HI, HF, $HNO_3$, $H_2SO_4$ ($SO_4^{--}$); $H_3PO_4$ ($HPO_4^{--}$); $H_2CO_3$, ($CO_3^{--}$); HSCN; camphor sulphonic acid, aliphatic or aromatic sulphonic acids, for example $C_1$-$C_6$-alkylsulphonic acids (for example methane sulphonic acid, ethane-, propane- or hexane sulphonic acid), benzene- or naphthalene sulphonic acid, which are optionally mono- or di-substituted by methyl groups (toluene sulphonic acid, in particular o- or p-toluene sulphonic acid), aliphatic $C_1$-$C_{20}$-monocarboxylic acids, in particular $C_1$-$C_{18}$-monocarboxylic acids, which are optionally mono-, di- or tri-substituted by halogen atoms (in particular Cl, F) (for example formic acid, acetic acid, propionic acid, palmitic acid, stearic acid, chloracetic acid, dichloracetic acid, trifluoracetic acid, trichloracetic acid); aliphatic $C_2$-$C_{11}$-dicarboxylic acids which optionally contain a double bond (for example oxalic acid, malonic acid, 2-amino-malonic acid, malonic acid substituted in the 2-position by a benzyl group or one or two $C_1$-$C_4$-alkyl groups, maleic acid, fumaric acid, succinic acid); aliphatic monohydroxy- and dihydroxymonocarboxylic acids with 2 to 8, in particular 2 to 6 carbon atoms, preferably being α-monohydroxycarboxylic acids such as lactic acid, glyceric acid or glycolic acid; di- and tricarboxylic acids having 3 to 8 carbon atoms, in particular 3 to 6 carbon atoms (for example malic acid, tartaric acid, malonic acid) which may also be substituted at one carbon atom by a hydroxy group and/or optionally by a $C_1$-$C_4$-alkyl group (isocitric acid, citric acid); phthalic acid which is optionally substituted by a carboxy group (in particular in the 4-position); gluconic acid, glucuronic acid; azetidinecarboxylic acid; squaric acid (3,4-dihydroxy-3-cyclobutene-1,2-dione); natural α-amino acids (for example L-asparaginic acid); 1,1-' cyclobutanedicarboxylic acid; organophosphoric acids such as aldose- and ketosephosphoric acids (for example the corresponding mono- and diphosphoric acids) for example aldose-6-phosphoric acids such as D- or L-glucose-6-phosphoric acid, α-D-glucose-1-phosphoric acid, D-fructose-6-phosphoric acid, D-galactose-6- phosphoric acid, D-ribose-5-phosphoric acid, D-fructose-1,6-diphosphoric acids; glycerophosphoric acids (where the phosphoric acid radical is bound to one of the end or to the central glycerine oxygen atom) such as α-D,L-glycerophosphoric acid, β-glycerophosphoric acid; N-phosphono-acetyl-asparaginic acid.

X preferably represents chlorine, bromine, iodine or —SCN (rhodanide) or the anion X is derived from a hydroxycarboxylic acid of the structure $R_5$—CH(OH)—$(CH_2)_n$—$CO_2H$, in which n can assume the values 0, 1, 2, 3 or 4 and $R_5$ represents hydrogen, halogen, hydroxy, $C_2$–$C_6$-alkanoyloxy, $C_1$–$C_6$-alkoxy, $C_1$–$C_6$-alkyl or phenyl, which is optionally substituted by halogen, hydroxy, $C_1$–$C_6$-alkoxy, $C_1$–$C_6$-alkyl or $C_1$–$C_6$-alkanoyloxy.

In the case of an oxycarboxylic acid of this type, the complex portion

has the following structure.

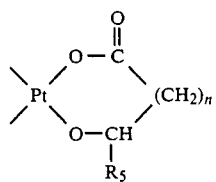

X is preferably derived from lactic acid or glycolic acid (in each case the racemate, the D-form or the L-form).

Other acids for the anions X may be: aromatic carboxylic acids containing one or several carboxy groups as well as, in addition, one or several (for example one, two, three, four or five) $C_1$–$C_4$-alkoxy groups and/or hydroxy groups. Should there be several carboxy groups on the aromatic radical (for example benzene ring), at least 2 carboxy groups should preferably be next to each other in adjacent positions. Should the benzene ring contain for example 4 or 5 carboxy groups, complexes may be formed which contain 2 moles of the platinum component per 1 mole of the benzenecarboxylic acid anion. Two neighboring carboxy groups in each case neutralize 1 mole of the platinum component so that, for example, in the case of benzenepentacarboxylic acid, the carboxy groups in the 1- and 2-positions as well as the 4- and 5-position carboxy groups in each case saturate 1 mole of the platinum components (i.e. 2 moles, taken together), whereas the carboxy group in the 3-position is present as free acid or in the form of a salt with a physiologically acceptable cation (for example an alkali cation, in particular the sodium cation). This applies quite generally when the anions X have additional acid functions which are not needed for the saturation of the platinum. The analogous situation applies in the case of the benzenehexacarboxylic acid where 1 mole of this acid may optionally saturate 3 moles of the platinum component.

Examples of acids of this type are: benzenemonocarboxylic acid, benzenedicarboxylic acids, benzenetricarboxylic acids (for example trimellitic acid), benzenetetracarboxylic acids, benzenepentacarboxylic acid, benzenehexacarboxylic acid; syringic acid, orotic acid.

Acids forming the X anions may also be amino acids or amino acid derivatives, the basic amino group of which is protected by an acid group. For example, amino acids having the following structure:

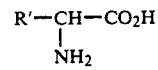

wherein R' represents hydrogen, a phenyl radical, an indolyl-(3)-methyl radical, imidazolyl-(4)-methyl radical, a $C_1$–$C_{10}$-alkyl group or a $C_1$–$C_{10}$-alkyl group substituted by a hydroxy group, a carboxy group, a $C_1$–$C_6$-alkoxy group, a mercapto group, a $C_1$–$C_6$-alkylthio group, a phenyl group, a hydroxyphenyl group, a $C_2$–$C_6$-alkanoylamino group or a $C_1$–$C_6$-alkoxycarbonyl group.

The basic amino group in the 2-position is protected (acylated) in this case by a conventional amino acid protecting group, for example by a $C_2$–$C_6$-alkanol radical or by a butyloxycarbonyl radical.

If R' in the above formula is an alkyl group, this is preferably a $C_1$–$C_6$-alkyl group which contains for example a $C_2$–$C_6$-alkanoylamino group, an imidazolyl-(4)-methyl radical or an indolyl-(3)-methyl radical in the 2-, 3-, 4-, 5- or 6-position (numbering begins at the position on the radical occupied by the alkyl radical). Individual examples of such amino acids are: leucine (preferably D- or L-form), valine (preferably D- or L-form), phenylalanine (preferably D- or L-form), phenylglycine (preferably D- or L-form), alanine (preferably D- or L-form), isoleucine (preferably D- or L-form), asparagine (preferably D- or L-form), lysine (preferably D- or L-form), tryptophan (preferably D- to L-form), tyrosine (preferably D- or L-form), ornithine (preferably D- or L-form), hydroxyproline (D- or L-form).

In this case the basic amino groups are blocked by a conventional acylamino protecting group, in particular by the acetyl group, chloroacetyl group or the butyloxycarbonyl group.

The corresponding acid addition salts may optionally also be prepared using physiologically acceptable acids, if the exchange groups X contain basic groups (for example amino groups).

Should X represent a water molecule, the acids mentioned, in particular strong acids, preferably $H_2SO_4$, may be used to neutralize the positive charge of the platinum atom.

The formula I' or I" also covers possible enantiomers and diastereomers. Should the compounds be racemates, these can be separated into the optically active isomers in known manner, for example using an optically active acid or using chiral phases. It is, however, also possible to use enantiomeric or optionally also diastereomeric starting substances from the outset, a correspondingly pure, optically active or diastereomeric compound then being obtained as the end product. Independently of the structure of the radical X, the cyclobutane part also optionally contains asymmetrical carbon atoms and can therefore be present in the racemate form or in an optically active or diastereomeric form.

Additional forms arise as a result of the stereochemistry of cyclobutane where the two aminomethyl groups as well as the radicals $R_1$ to $R_4$ can be arranged in the cis- or trans-positions. Furthermore, additional forms can be produced by various enantiomeric or diastereomeric forms of the radicals X.

With regard to the platinum atom in the compounds of the invention of formula I' or I" it is in particular the cis-compounds that are involved.

The invention also includes a process for making the compounds I' in which a tetrahalogeno-platinum(II) acid, a tetrahalogeno-platinum(II)-complex salt with two monovalent or one bivalent cations or a platinum-(II)-halide is reacted with a compound of formula

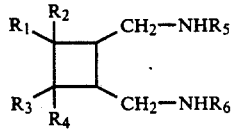

II or a salt of compound II with a physiologically acceptable ion of opposite charge or an acid addition salt of compound II, in which the radicals $R_1$ to $R_6$ have the meanings given and optionally exchanging the radical X or the radicals X in a so obtained compound of formula I for other physiologically acceptable anions and/or optionally converts compounds so obtained into the salts with physiologically acceptable anions or cations.

The starting amine II is for example used as racemate, as purely the right- or left-rotating form, as the cis- or trans-form (in relation to the position of the aminomethyl groups) or in another diastereomeric form.

These configurations are maintained during the preparation of the platinum complex.

The process for the preparation of the compounds I' of the invention is preferably carried out in a solvent at temperatures between 10° and 80° C., preferably 20° to 40° C., in particular 25° to 30° C. The solvent may, for example, be: water, $C_1$–$C_6$-alkanols (methanol, ethanol, tert-butanol), cyclic ethers such as tetrahydrofuran, dioxane, saturated ethers of mono- or polyvalent alcohols such as ethyleneglycoldimethyl ether, diethyleneglycoldimethyl ether, lower saturated ketones (acetone, methyl ethyl ketone), aprotic agents such as dimethyl sulphoxide or dialkylamides of lower aliphatic carboxylic acids (formic acid, acetic acid) with $C_1$–$C_6$-alkyl radicals such as dimethyl formamide, dimethyl acetamide as well as mixtures of these solvents, in particular mixtures with water.

The two reaction components (platinum compound and compound II) are preferably used in equimolar amounts. The pH of the reaction solution should be between 6 and 9, preferably around pH 8. The adjustment of the pH is in particular effected by addition of alkali, preferably aqueous sodium hydroxide solution or potassium hydroxide solution or for example also by means of sodium carbonate or through the addition of acids, preferably aqueous hydrochloric acid. The adjustment of the pH can also be effected by means of ion exchangers.

Tetrahalogen-platinum(II) compounds (acid as well as complex salts) that may be used are the corresponding tetrachloro-, tetrabromo- and tetraiodo compounds. Should platinum(II) halides be used as the starting components, the halogen atoms are the same.

Monovalent cations which may be used are: alkali ions, in particular sodium and potassium; it is, however, also possible to use lithium, rubidium, caesium as well as $NH_4^+$, $NR_4^+$, $PR_4^+$ or $AsR_4^+$, in which R is a $C_1$–$C_6$-alkyl radical or a phenyl radical. Bivalent cations may be: alkaline earth ions, in particular $Mg^{2+}$ and $Ca^{2+}$, but also $Zn^{2+}$. Platinum(II)-halides may, for example, be $PtCl_2$, $PtBr_2$ and $PtI_2$.

The compound II is either used in the form of the diamine or in the form of an acid addition salt: for example as monohydrochloride or dihydrochloride, mono- or dihydrobromide, mono- or dihydroiodide or as a salt with another conventional inorganic or organic acid. It is in particular also possible to use acids, the anions of which form the radicals X. The diamine may, moreover, be used in the form of the acetate or diacetate, potassium chloride optionally being added before mixing of the reaction components (for example 2 mole per 1 mole of compound II). In addition the diamine II may, for example, be used in the form of the hydrochloride, carbonate, oxalate or malonate.

The invention also includes a process for making compounds of the formula I" wherein a compound of the formula I' is oxidized, optionally in the presence of a compound HX, and one or several of the radicals X in the thereby obtained reaction product is optionally exchanged for other physiologically acceptable anions and/or optionally the obtained compounds are converted into the salts with physiologically acceptable anions or cations.

The process for the preparation of the platinum(IV) complexes of formula I" is effected, for example, in the same media as in the case of the process for the preparation of the platinum(IV) complexes of formula I'. These conversions are effected at a temperature in the range between 20° and 100° C., preferably 40°–80° C. Oxidizing agents which may be used are: halogens such as chlorine gas, bromine, iodine, hydrogen peroxide (for example 3 to 60%; preferably 10 to 40%, in particular 35%), dirhodan (gaseous), hydrohalic acids (HCl, HBr, HI). Should oxidation be effected with halogen, dirhodan or halohydric acids, the optional additional presence of a compound HX is not necessary.

The exchange of the ligands X for other ligands may, for example, be effected by means of silver halide precipitation. For example, a dihalogeno-1,2-bis(aminomethyl)cyclobutane-platinum(II) compound of formula I' or optionally also a compound of formula I", wherein X represents halogen (chlorine, bromine or iodine) is reacted in a solution or suspension agent at temperatures between 0° to 90° C., preferably 10° to 50° C., in particular 30° to 40° C., preferably 40° C., with the silver salts of a different acid which corresponds to the meaning X. Silver nitrate (for example aqueous silver nitrate solution) may also be used as the silver salt to obtain (if the starting material is a compound I') an ionic dihydro complex of the formula

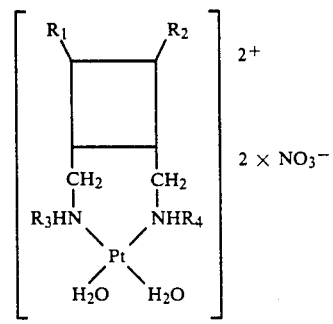

From this complex it is possible to displace the weakly bound water ligand with anions having greater affinity (for example $Cl^-$, $Br^-$ in the form of NaCl, KCl, NaBr, KBr, malonate$^{2-}$, chloracetate(-), oxalate$^{2-}$, 1,1-cyclobutanedicarboxylic acid anion$^{2-}$ as well as the other acid radicals X referred to, used in the form of the acids or their salts, in particular their alkali salts.

The same compounds may also be obtained by treatment of the previously mentioned dihydro-nitrate complex with an anion exchanger in the hydroxide form (for example Dowex 1-8×), whereby the 2 molecules of water are replaced by OH and subsequent reaction of the complex compound so obtained (X=OH in each case) with the equimolar amount of HX where X is a physiologically acceptable acid anion.

An exchange of the leaving group (for example $SO_4^{2-}$ or oxalate anion$^{2-}$) is also possible in the case of the sulphato- or oxalato-1,2-bis(aminomethyl)-cyclobutane-platinum(II) compounds by reaction with alkaline earth salts which contain the desired, X-ligands (for example glyceric acid), provided the complex formed is soluble in water and thus permits the separation of the alkaline earth sulphate or oxalate which possess poor solubility in water.

X-ligands suitable for this process are preferably the anions of hydroxycarboxylic acids, sulfonic acids, haloacetic acids, nitric acid.

The solution or suspension agents which are listed for the process of the preparation of compounds I may also be used for the exchange reaction (water, dimethyl formamide, dimethylacetamide, dimethyl sulphoxide, methanol, ethanol, tert-butanol, acetone, methyl ethyl ketone). The exchange reaction is, for example, carried out in a pH range between 3 and 9.

The preparation of unknown starting amines of formula II can be effected for example as described in example I from the corresponding known cyclobutane-1,2-dicarboxylic acids (with the substituents $R_1$ and $R_2$ in the 3-position as well as $R_3$ and $R_4$ in the 4-position.

The cyclobutane-1,2-dicarboxylic acid substituted in the cyclobutane ring by the radicals $R_1$, $R_2$, $R_3$ and $R_4$ is converted into the corresponding amide via the corresponding acid dihalide (chloride, bromide) using ammonia or an amine $NHR_5$ or $NHR_6$ in known manner and this is then reduced in the manner known for this purpose by means of hydration (for example catalytic hydration or by means of complex hydrides such as LiAlH$_4$) into the diamine of formula II.

In addition, it is possible to prepare starting amines of this type according to the following methods: catalytic hydration of corresponding dicyano compounds in the presence of metal catalysts conventionally used therefor according to British patent No. 1,121,413; reduction of the lithium aluminum hydride in diethylether or tetrahydrofuran; conversion into the corresponding acid amides using formic acid/HCl and subsequent reduction with lithium aluminum-hydride in tetrahydrofuran; Curtius degradation of the corresponding acid azides; degradation according to the method of K. F. Schmidt (see for example J. Am. Soc. 64 (1942), pages 269-98).

The amino substituents $R_5$ and/or $R_6$ are introduced by starting with the synthesis of diamines II having the appropriate amino substituents. For further information reference is made to the preparation of some starting compounds of formula II in the examples.

The compounds of the invention display a good antitumor activity, for example against P388 leukemia in the mouse.

For example, with the above mentioned experimental method an intraperitoneal dose of 10-30 mg/kg body weight of mouse achieved a 77% prolongation of survival time. The lowest effective dose in the above mentioned animal experiment is for example 2 mg/kg orally
0.5 mg/kg intraperitoneally
0.5 mg/kg intravenously The general dosage range for the effect (animal experiment as above) may for example be:

2-2000 mg/kg orally, in particular 50-200 mg/kg
0.5-1000 mg/kg intraperitoneally, in particular 2-100 mg/kg
0.5-1000 mg/kg intravenously, in particular 2-100 mg/kg The action of the compounds of the invention is comparable with the action of the known medicinally active substance cis-platinum, the following differences however being apparent: better efficacy, different spectrum of action, virtually no nephrotoxicity.

Indications that could be considered for the compounds of the invention are: chemotherapy of malignant disorders (cancer). The kinds of human cancer for which the platinum complexes are considered useful include tumors in the male testicles, prostate cancer, ovarian carcinoma, carcinoma of the uterus and head and neck tumors.

The pharmaceutical formulations contain in general between 1 to 2000, preferably 10 to 1000 mg of the active component(s) of the invention.

Administration may, for example, be in the form of tablets, capsules, pills, sugar-coated tablets, suppositories, ointments, gels, creams, powders, dusting powders, aerosols or in liquid form. Liquid forms of application that may, for example, be used include: oily or alcoholic or aqueous solutions as well as suspensions and emulsions. Preferred forms of application are tablets which contain between 100 and 1000 mg or lyophilizates (for example for the preparation of solutions) containing between 10 and 200 mg of active substance.

The individual dose of the active components of the invention may, for example, lie a) between 10 and 2000 mg, preferably 10 to 1000 mg, in the case of oral medicinal forms;
b) between 1 and 1000, preferably 5 to 200 mg, in the case of parenteral medicinal forms (for example intravenous, intramuscular).

It is, for example, possible to recommend 1 to 4 tablets containing between 10 and 500 mg of active substance 3 times daily or, for example for intravenous injection, one ampoule with 1 to 200 mg of substance 1 to 4 times daily. In the case of oral administration the minimum daily dose is for example 1 mg; the maximum daily dose for oral administration should not exceed 2000 mg.

For the treatment of dogs and cats the individual oral dose generally lies between about 10 and 500 mg/kg body weight; the parenteral dose is between about 1 and 500 mg/kg body weight.

For the treatment of horses and cattle, the oral dose generally lies between about 10 and 500 mg/kg; the parenteral individual dose between about 1 and 500 mg/kg body weight.

The acute toxicity of the compounds of the invention in the mouse (expressed by the LD 50 mg/kg; method of Miller and Tainter: Proc. Soc. Exper. Biol. a. Med. 57 (1944) 261) lies, for example, between 5 and 1000 mg/kg in the case of intraperitoneal administration.

The medicaments may be used in human medicine, in veterinary medicine and in agriculture, alone or in mixtures with other pharmacologically active substances.

The compounds of the invention are suitable for the preparation of pharmaceutical formulations. The pharmaceutical formulations or medicaments may contain one or several of the compounds of the invention or also mixtures thereof with other pharmaceutically active substances. For the preparation of the pharmaceutical formulations it is possible to use conventional pharmaceutical carrier and auxiliary substances. The medicaments may, for example, be administered enterally, parenterally (for example intravenously, intramuscularly, intraperitoneally, subcutaneously) or orally. Administration may, for example, be in the form of tablets, capsules, pills, sugar-coated tablets or suppositories. Liquid formulations may, for example, be oily or aqueous solutions or suspensions (for example in sesame or olive oil), emulsions, injectable aqueous and oily solutions or suspensions. Furthermore it is, for example, possible to prepare dry ampoules containing compound I of the invention as active substance, the contents of such dry ampoules being, for example, dissolved in physiologically saline solution or mixtures of physiological saline solution and, for example, dimethyl sulphoxide.

DETAILED DESCRIPTION OF PREFERRED EMBODIMENTS

Example 1

Dichloro-1,2-bis(aminomethyl)cyclobutane-platinum-(II)

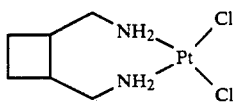

0.81 g (0.014 mol) of KOH and 1.5 g (0.0073 mol) of 1,2-bis(aminomethyl)cyclobutane are added to a solution of 3.05 g (0.0073 mol) of potassium tetrachloroplatinate in 10 ml of water at a temperature of 50° C. and stirred for 3 hours. After cooling to room temperature the mixture is suction filtered, washed with water and with acetone/diethylether 1:1. Yield: 1.0 g Melting point: 225°–226° C. (decomposition)

Preparation of the starting amine II

A) 5 g (0.028 mol) of trans-cyclobutane-1,2-dicarboxylic acid dichloride are added dropwise to a mixture of 50 ml of concentrated ammonia solution and 50 ml of ice. After addition, the mixture is stirred for one hour after which the precipitate (acid amide) is suction filtered, washed with water and recrystallized from 150 ml of ethanol (Yield: 2.5 g).

Melting point: 231°–233° C.

The acid amide thereby obtained is then reduced with lithium aluminum hydride to the diamine II: 8 g (0.21 mol) of lithium aluminum hydride are suspended in a nitrogen atmosphere in 200 ml of anhydrous tetrahydrofuran. At a temperature of 0° C. 5 g (0.035 mol) of amide are carefully added in portions. When all has been added, stirring continues for a further hour at room temperature and the mixture is then heated under reflux for 4 hours. It is left to stand overnight. First ethyl acetate and then water is added and the precipitate is then separated by means of filtration. The filtrate is dried over magnesium sulphate and concentrated in a rotary evaporator. The residue is taken up with isopropyl alcohol and the salt precipitated with 7 g (0.07 mol) of oxalic acid and recrystallized from ethanol. (Yield: 4.7 g). The dioxalate melts at 160° C. with decomposition.

B) 115 g (3 mol) of $LiAlH_4$ are treated with a solution of 53 g (0.5 mol) of 1,2-dicyanocyclobutane (dissolved in 500 ml of diethyl ether) at −10° C. in 1500 ml of diethyl ether. The mixture is left to stand overnight and then hydrolyzed with 185 ml of ethyl acetate and 350 ml of water. The precipitate is suction filtered, washed with ether and the filtrate concentrated to dryness in a rotary evaporator.

There are obtained 38 g of 1,2-bis(aminomethyl)cyclobutane which is dissolved in 550 ml of ethanol and mixed with 50.4 g of oxalic acid. The precipitate is suction filtered and washed with a little ether. 68 g of dioxalate are obtained. Melting point: 160° C. (decomposition).

Representation of the lactato complex (Example 1a)

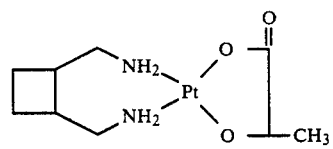

3.8 g (0.01 mol) of chloro complex are suspended in 20 ml of water and heated to 40° C. 3.39 g (0.02 mol) of silver nitrate are added and stirred for 1.5 hours. The mixture is left to cool in a refrigerator. The silver nitrate precipitate is then suction filtered and washed with 10 ml of water. The filtrate is passed through a column containing 100 ml of a basic ion exchanger and dropped into 1 g (0.01 mol) of L-lactic acid. After stirring for 3 days at room temperature the mixture is concentrated, the residue is dissolved in methanol and stirred with addition of activated charcoal. After filtration, the mixture is reacted with diethyl ether until it becomes cloudy and left to crystallize overnight in a refrigerator. The crystals collected on the sintered glass after suction filtration are washed with diethyl ether and dried at 40° C. Yield: 1.2 g Melting point: 220° C. (decomposition).

Examples of additional complexes of the 1,2-bis(aminomethyl)-cyclobutane-platinum(II) with various anions X General method of preparation 3.8 g (0.01 mol) of dichloro-1,2-bis(aminomethyl)cyclobutane platinum(II) are suspended in 20 ml of water to which 1 ml of ethanol has been added and treated with 3.39 g (0.02 mol) of $AgNO_3$. After heating to 40° C. the mixture is stirred at the given temperature for about 5 hours. After cooling to 15° C. (in a refrigerator) the precipitated AgCl is filtered off and the residue is washed with 10 ml of water. After passing dropwise over a column containing 100 ml of basic ion exchanger (OH type) the filtrate is then allowed to flow into a solution of 0.01 mol of the new leaving group (X) in 5 ml of water. The mixture thereby obtained is stirred overnight and then concentrated and purified by means of column chromatography from acetone/water.

The complexes obtained are listed in Table 1:

TABLE 1

| Structural part $\diagup Pt \diagdown^X_X$ and Acid used | | Yield | |
|---|---|---|---|
| (b) D,L-2-Hydroxy-3-methylbutyric acid | | 1.9 g | White powder Rf-value: 0.44 Silica gel acetone/water 4:1 |
| (c) 2-Hydroxy-2-methylbutyric acid | | 1.95 g | White powder Melting point 202–203° C. |
| (d) Glycolic acid | | 1.6 g | White powder Melting point 250–251° C. |
| (e) L(−)-3-Phenyl lactic acid | | 2.5 g | Melting point 195–196° C. |
| (f) L-Ascorbic acid | | 2.0 g | Melting point 203–210° C. |
| (g) Maleic acid | | 2.9 g | Rf-value: 0.33 Silica gel acetone/water 4:1 |
| (h) Malonic acid | | 2.5 g | Rf-value: 0.41 Silica gel propanol/water 5:1 |
| (i) Oxalic acid | | 2.6 g | Rf-value: 0.38 Silica gel acetone/water 4:1 |
| (j) Sulphuric acid | | 2.8 g | Melting point 280–284° C. |
| (k) Palmitic acid | | 3.2 g | Melting point 75–80° C. |
| (l) 1,2,3-Propanetricarboxylic acid | | 2.4 g | Melting point 253–255° C. |
| (m) N-Acetyl-alanine | | 2.15 g | Melting point 88–92° C. |
| (n) D,L-2-Hydroxyhexane acid | | 2.2 g | Melting point 187–189° C. |
| (o) Cyclobutane-1,1-dicarboxylic acid | | 1.8 g | Melting point 240–245° C. |

The preparation of the complex according to m) is carried out according to the following procedure:

2.9 g of dichloro-1,2-bis(aminomethyl)cyclobutane-platinum(II) are suspended in 50 ml of water and treated with 2.6 g of silver nitrate. After stirring for 4 hours at 50° C. the silver chloride precipitate is removed by suction filtering, the colorless filtrate is treated with 2 g of N-acetylalanine and 0.85 g of KOH and stirring is continued for a further 5 hours at 30° C. The reaction mixture is freeze dried and the residue recrystallized from ethanol.

Example 2

Dichloro-1,2-bis(methylaminomethyl)cyclobutane-platinum(II)

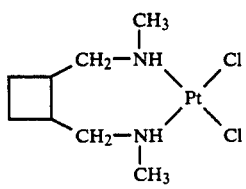

1.79 g (0.0043 mol) of potassium tetrachloroplatinale II are dissolved in 5 ml of water at 50° C. and treated with 0.5 g (0.0086 mol) of KOH and 1 g (0.0043 mol) of 1,2-bis(methylamino-methyl)-cyclobutane. After stirring for 2 hours the mixture is cooled to room temperature and suction filtered.

Yield: 0.53 g

The starting amine may, for example, be obtained as follows:

10 g of cyclobutane-1,2-dicarboxylic acid dichloride are added dropwise with ice cooling into 200 ml of saturated methylamine solution. After stirring for 4 hours at room temperature the mixture is concentrated in a rotary evaporator and the residue recrystallized from 900 ml of ethyl acetate.

5.6 g of methyl cyclobutane-1,2-dicarboxylamide are obtained.

(Melting point: 180°–181° C.).

5.3 g (0.031 mol) of the amide so obtained are added in small portions to 7.06 g (0.186 mol) of LiAlH$_4$ in 173 ml of tetrahydrofuran (cooled in an ice bath). After stirring for one hour and further addition of 93 ml of tetrahydrofuran the mixture is heated under reflux. After being allowed to stand overnight the mixture is first mixed with ethyl acetate under ice cooling and then water is added. After stirring for one hour the mixture is filtered and dried over K$_2$CO$_3$ and concentrated in a rotary evaporator. The residue is taken up with ethanol and treated with 6.5 g of oxalic acid (dissolved in 20 ml of water). The precipitated product is recrystallized once from ethanol. The oxalate (2 mol of oxalic acid to one mol of amine) melts at 145°–147° C. (1.3 g).

Example 3

Pt(IV) complex

Dichloro-dihydroxy[1,2-bis(aminomethyl)cyclobutane]-platinum(IV)

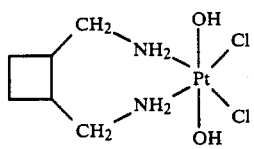

0.5 g (0.0013 mol) of dichloro-1,2-bis(aminomethyl)-cyclobutane-platinum(II) are suspended in 10 ml of water at 70° C. and treated dropwise with 5 ml of H$_2$O$_2$ (35% solution). The mixture is stirred for 4 hours at 70° C. (pH 4) and left in a cold place overnight. The orange-yellow precipitate is suction filtered and washed with a little water. The filtrate is treated with 200 ml of platinum activated charcoal to remove the unused hydrogen peroxide and stirred at room temperature for 3 hours, after which the platinum activated charcoal is suction filtered. The filtrate is concentrated to dryness.

Yield: 200 mg of yellow powder.

Example 4

Pt(IV) complex

Tetrachloro-[1,2-bis(aminomethyl)cyclobutane]-platinum(IV)

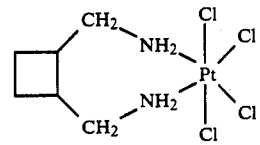

2 g (0.0053 mol) of dichloro-1,2-bis(aminomethyl)cyclobutane-platinum(II) are suspended in 250 ml of water and reacted with chlorine gas at room temperature. Chlorine gas is introduced for 4 hours. A solution is formed from which an orange-yellow product is precipitated which is suction filtered during the further course of the reaction, washed with water and dried at 40° C. in a vacuum.

Yield: 0.85 g.

Example 5

Pt(IV)-complex

Dihydroxy-lactato-[1,2-bis(aminomethyl)cyclobutane]-platinum(IV)

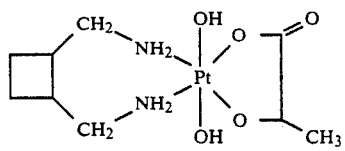

0.5 g of lactato-[1,2-bis(aminomethyl)cyclobutane]-platinum(II) are dissolved in 10 ml of water at 70° C. and treated with 5 ml of H$_2$O$_2$ solution (35%). After stirring for 4 hours at 70° C. (pH 5) the mixture is allowed to cool overnight. The excess H$_2$O$_2$ is treated with platinum activated charcoal, the activated charcoal is filtered off and the filtrate is evaporated to dryness.

Yield: 200 mg of yellow powder.

EXAMPLES OF PHARMACEUTICAL FORMULATIONS

Examples of capsules 1 kg of lactato complex according to Example 1a, 625 g of microcrystalline cellulose and 11 g of highly dispersed silicon dioxide are passed through a sieve of mesh size 0.8 mm and homogenized. 39 g of magnesium stearate (sieved 0.8 mm) are then added to this mixture and mixed again for 1 minute.

To prepare the capsules the capsule mass is filled in known manner into hard gelatin capsules of size 00 in a capsule machine fitted with size 00 molds. The filling amount per capsule is 670 mg, corresponding to 400 mg of active substance.

Example for lyophilizate 20 g of lactato complex according to Example 1a are dissolved with stirring in 900 ml of water for injection purposes. The result is then made up to 1 liter with water for injection purposes.

This solution is sterile filtered using a membrane filter of 0.22 μm pore size and filled in 2 ml portions into 10 ml injection bottles of hydrolytic class I. The bottles are provided with a freeze drying stopper and freeze dried in a suitable apparatus. After drying, sterile, dried nitrogen is passed though and the bottles are sealed in the apparatus. The stoppers are secured with a close-fitting top.

For intravenous application the lyophilizate is dissolved in 4 ml of water for injection purposes. 1 injection bottle contains 40 mg of the substance of Example 1a, 1 ml of solution contains 10 mg of active substance.

What is claimed is:

1. 1,2-Bis(aminomethyl)cyclobutane-platinum compounds having general formula:

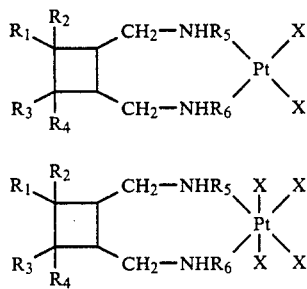

wherein the radicals, $R_1$, $R_2$, $R_3$, $R_4$, $R_5$ and $R_6$ are the same or different and are selected from the group consisting of hydrogen; $C_1$–$C_6$-alkyl; phenyl; phenyl-$C_1$–$C_6$-alkyl; $C_1$–$C_6$-alkyl which is substituted with halogen, hydroxy, $C_2$–$C_6$-alkanoyloxy or $C_1$–$C_6$-alkoxy; phenyl which is substituted with halogen, hydroxy, $C_2$–$C_6$-alkanoyloxy or $C_1$–$C_6$ alkoxy; and phenyl-$C_1$–$C_6$-alkyl in which the phenyl group is substituted with halogen, hydroxy, $C_2$–$C_6$-alkanoyloxy or $C_1$–$C_6$-alkoxy and wherein x comprises a physiologically acceptable and pharmaceutically useful anion of single or multivalent acids, or a hydroxy anion.

2. 1,2-Bis(aminomethyl)cyclobutane-platinum compounds as set forth in claim 1, wherein the physiologically acceptable and pharmaceutically useful anions are the anions of single or multivalent acids selected from the group consisting of HBr, HCl, HI, $HNO_3$, $H_2SO_4$, $H_3PO_4$, $H_2CO_3$, and HSCN.

3. 1,2-Bis(aminomethyl)cyclobutane-platinum compounds as set forth in claim 1, wherein the physiologically acceptable and pharmaceutically useful anions are the anions of single or multivalent acids selected from the group consisting of unsubstituted benzene- or naphthalene sulphonic acids and substituted benzene- or naphthalene sulfonic acids which are mono- or di-substituted by methyl groups.

4. 1,2-Bis(aminomethyl)cyclobutane-platinum compounds as set forth in claim 1, wherein the physiologically acceptable and pharmaceutically useful anions are the anions of aliphatic $C_1$–$C_{20}$-monocarboxylic acids.

5. 1,2-Bis(aminomethyl)cyclobutane-platinum compounds as set forth in claim 4, wherein the aliphatic $C_1$–$C_{20}$-monocarboxylic acids are $C_1$–$C_{18}$-monocarboxylic acids.

6. 1,2-Bis(aminomethyl)cyclobutane-platinum compounds as set forth in claim 1, wherein the physiologically acceptable and pharmaceutically useful anions are the anions or single or multivalent acids selected from the group consisting of aliphatic $C_2$–$C_{11}$-dicarboxylic acids which are saturated or contain a carbon-carbon double bond.

7. 1,2-Bis(aminomethyl)cyclobutane-platinum compounds as set forth in claim 1, wherein the physiologically acceptable and pharmaceutically useful anions are the anions of single or multivalent acids selected from the group consisting of aliphatic monohydroxy- and dihydroxymonocarboxylic acids with 2 to 8 carbon atoms.

8. 1,2-Bis(aminomethyl)cyclobutane-platinum compounds as set forth in claim 7, wherein the aliphatic monohydroxy- and dihydroxymonocarboxylic acids contain 2 to 6 carbon atoms.

9. 1,2-Bis(aminomethyl)cyclobutane-platinum compounds as set forth in claim 8, wherein the aliphatic monohydroxycarboxylic acids are α-monohydroxycarboxylic acids.

10. 1,2-Bis(aminomethyl)cyclobutane-platinum compounds as set forth in claim 1, wherein the physiologically acceptable and pharmaceutically useful anions are the anions of acids selected from the group consisting of unsubstituted dicarboxylic acids having 3 to 8 carbon atoms or unsubstituted tricarboxylic acids having 4 to 8 carbon atoms or dicarboxylic acids having 3 to 8 carbon atoms or tricarboxylic acids having 4 to 8 carbon atoms which are substituted by a hydroxy group or a $C_1$–$C_4$-alkyl group.

11. 1,2-Bis(aminomethyl) cyclobutane-platinum compounds as set forth in claim 10, wherein the unsubstituted dicarboxylic acids contain 3 to 6 carbon atoms and the tricarboxylic acids contain 4 to 6 carbon atoms.

12. 1,2-Bis(aminomethyl)cyclobutane-platinum compounds as set forth in claim 1, wherein the physiologically acceptable and pharmaceutically useful anions are the anions of single or multivalent acids selected from the group consisting of unsubstituted phthalic acid and phthalic acid which is substituted by a carboxy group.

13. 1,2-Bis(aminomethyl)cyclobutane-platinum compounds as set forth in claim 1, wherein the physiologically acceptable and pharmaceutically useful anions are the anions of single or multivalent acids selected from the group consisting of gluconic acid, glucuronic acid, azetidinecarboxylic acid, squaric acid, natural α-amino acids and 1,1-cyclobutanedicarboxylic acid.

* * * * *